United States Patent [19]

Möller et al.

[11] Patent Number: 4,528,286
[45] Date of Patent: Jul. 9, 1985

[54] METHOD OF USING CERTAIN ARYL-MERCAPTO-LOWER-ALKANAMIDES AS ANTISEBORRHEIC AGENTS

[75] Inventors: Hinrich Möller; Siegfried Wallat, both of Monheim, Fed. Rep. of Germany

[73] Assignee: Henkel Kommanditgesellschaft (KGaA), Duesseldorf, Fed. Rep. of Germany

[21] Appl. No.: 444,588
[22] PCT Filed: May 21, 1982
[86] PCT No.: PCT/EP82/00111
§ 371 Date: Nov. 15, 1982
§ 102(e) Date: Nov. 15, 1982
[87] PCT Pub. No.: WO82/04391
PCT Pub. Date: Dec. 23, 1982

[30] Foreign Application Priority Data

May 27, 1981 [DE] Fed. Rep. of Germany ....... 3121072

[51] Int. Cl.³ .......................... A61K 7/06; A61K 7/48
[52] U.S. Cl. .................... 514/232; 514/319; 514/330; 514/346; 514/618; 546/226; 546/291; 564/162; 544/158; 548/179; 548/221
[58] Field of Search ................ 564/162; 424/324, 267, 424/248.52; 546/226; 544/158

[56] References Cited

PUBLICATIONS

Moeller, Chem. Abstracts, vol. 96, No. 5, Abst. No. 40931t, Feb. 1, 1982.

Kuwano et al., Chem. Abstracts, vol. 95, No. 9, Abst. No. 75,381v, Aug. 31, 1981.
Nordmann et al., Chem. Abstracts, vol. 71, No. 19, 91071d, Nov. 10, 1969.
Manoury et al., Chem. Abstracts, vol. 76, No. 5, Abst. No. 24,905u, Jan. 31, 1972.
De Marchi et al., Chem. Abstracts, vol. 68, No. 5, Abst. No. 21633c, Jan. 29, 1968.

Primary Examiner—Alan L. Rotman
Attorney, Agent, or Firm—Ernest G. Szoke; Nelson Littell, Jr.; Henry E. Millson, Jr.

[57] ABSTRACT

Aryl-mercapto-lower-alkanamides having the following formula

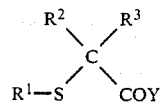

wherein $R^1$ is selected from the group consisting of phenyl, $C_{1-4}$-alkylphenyl, halophenyl, hydroxyphenyl, $C_{1-4}$-alkoxyphenyl, aminophenyl, acetamidophenyl, naphthyl, diphenyl; $R^2$ and $R^3$, independently represent hydrogen or $C_{1-14}$-alkyl; Y represents $NR^4R^5$ wherein $R^4$ and $R^5$ independently represent hydrogen, $C_{1-6}$-alkyl, $C_{2-3}$-hydroxyalkyl, benzyl, anilyl, and taken together represent piperidyl or morpholinyl are useful for reducing cell sebum production in a mammal in the form of a topical cosmetic preparation.

3 Claims, No Drawings

METHOD OF USING CERTAIN ARYL-MERCAPTO-LOWER-ALKANAMIDES AS ANTISEBORRHEIC AGENTS

The subject of the invention are topical, cosmetic preparations for the improvement of the oily and unesthetic appearance of hair and skin, especially for the treatment of very oily hair.

The excessive secretion of the seborrheic glands of the scalp gives the hair an oily appearance which is generally considered unesthetic. Consequently, many attempts were made to restore a healthy appearance to the hair by adjusting the secretion of the seborrheic glands to their normal level with suitable preparations. Oral preparations containing cysteamine derivatives were recommended for the treatment of seborrhea in the DE-OS No. 16 67 092. Shampoos with sulfur, mercury or tar additives were used to treat seborrhea of the hair on the head. It was observed that the extended use of these well-known products frequently led to side effects without producing actually satisfactory results with regard to efficacy or application technological properties. Finally, N,N-diethyl-m-toluamide was recommended as active substance for the treatment of dandruff due to seborrhea in the DE-OS No. 19 06 665. In the U.S. Pat. No. 3,755,604, phenyl-pentadienoic acids are recommended as agent for the prevention of the production of sebum. But it was found that neither N,N-diethyl-m-toluamide nor phenyl-pentadienoic acid has a satisfactory antiseborrheic effect.

Now, it was observed that topical cosmetic preparations with a content of compounds of the general formula:

in which $R^1$ represents an aryl radical or a heterocyclic radical, $R^2$ and $R^3$ represent independently of one another hydrogen or an alkyl group with 1 to 4 carbon atoms, and Y an alkoxy group with 1 to 12 carbon atoms, an aralkoxy group or an amino group $NR^4R^5$ in which $R^4$ and $R^5$ stand for hydrogen, an alkyl group with 1-6 carbon atoms, an aryl group or an aralkyl group or they can form a heterocyclic ring together with the nitrogen atom, are especially effective in the treatment of seborrheic skin and very oily hair. $R^1$ includes radicals of the general formula (II)

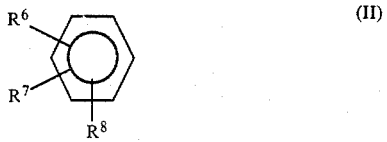

in which $R^6$, $R^7$ and $R^8$ represent independently of one another a hydrogen atom, an alkyl group with 1 to 4 carbon atoms, a halogen atom (especially Cl), an aryl group, a hydroxy group, an alkoxy group with 1 to 4 carbon atoms, or an amino group that may also be alkylated or acylated, and two of the radicals $R^6$–$R^8$, which, together with the benzene ring, stand for a naphthalene ring, and includes heterocyclic radicals such as a, if needed substituted, pyridyl, pyrimidyl, benzoxazolyl, benzimidazolyl or benzthiazolyl group.

Most compounds according to Formula (I) are known from the literature and most of them are commercially available. Arene-carboxylic acid derivatives are prepared suitably from the free arene-carboxylic acids, which are converted to esters or amides by a known method, using alcohols or amines. Synthesis of the carboxylic acid derivatives according to Formula (I) is also possible by alkylating the respective mercapto compounds with suitable a-halo-alkanoic acid derivatives.

Arene-carboxylic acids suitable as starting product are, for example: 2-(Phenyl-, 2-chlorophenyl-, 3-chlorophenyl-, 4-chlorphenyl-, 2,4-dichlorophenyl-, 3,4-dichlorophenyl-, 4-hydroxyphenyl-, 2,4-dihydroxyphenyl-, 3,4-dihydroxyphenyl-, 4-aminophenyl-, 4-acetamidophenyl-, 4-tolyl-, α-naphthyl-, β-naphthyl, 4-methoxyphenyl-, 2,4-dimethoxyphenyl-, 3,4,5-trimethoxyphenyl-, 2,4,6-trichlorophenyl-, benzoxazol-2-yl-, 5-chlorobenzoxazol-2-yl-, 5,7-dichlorobenzoxazol-2-yl, benzothiazol-2-yl-, 5-chlorobenzothiazol-2-yl, benzimidazol-2-yl-, 2-, 3-, 4-pyridyl-, N-oxido-2-pyridyl, 2-pyrimidyl-, 4-pyrimidyl-, 4,6-dihydroxy-2-pyrimidyl-mercapto)-acetic acid, -propionic acid, -butyric acid, -isobutyric acid and -2-ethylbutyric acid.

Suitable as alcohol component for the preparation of the arene-carboxylic esters are, for example, methanol, ethanol, propanol, isopropanol, N-butanol, isobutanol, sec-butanol, tert-butanol, pentanol, hexanol, octanol, 2-ethyl-hexanol, decanol, benzyl alcohol.

Suitable as amide component of the amides to be used according to the invention are, in addition to primary amides, for example, methyl-, dimethyl-, ethyl-, diethyl-, propyl-, dipropyl-, methyl propyl-, 2-propyl-, di-2-propyl-, butyl-, dibutyl-, 2-butyl-, sec-butyl-, tert-butyl-, hexyl-, dihexyl-, ethanol-, diisopropanol-amine, benzylamide, anilide, piperidide and morpholide.

The cosmetic agents according to the invention are solutions of the active compounds of Formula (I) to be used in water, in alcohol, in aqueous alcoholic mixtures, in oil, suspensions, gels, emulsions, ointments, pastes or aerosols. the antiseborrheic arene-carboxylic acid esters and amides can be incorporated in almost all cosmetic agents normally used for the treatment of skin and hair, for example in hair tonics, shampoos, hair treatments, hair rinses, or also in skin lotions and shaking mixtures. In addition to the compounds of Formula (I), the products according to the invention contain known vehicles and adjuvants such as water, organic solvents, surfactants, oils and fats, waxes, perfume oils, pigments, preservatives and similar substances. Shampoo is an advantageous form of application for the treatment of very oily hair. In addition to the sebosuppressive active agent, such shampoos may contain anionic, cationic, nonionic or amphoteric tensides, pigments, fragrances, thickeners or conditioners.

The cosmetic agents according to the invention contain the arene-carboxylic acid derivatives in an amount of 0.01 to 20 percent by weight, preferably 1 to 10 percent by weight, calculated with regard to the total product. The agents according to the invention can be applied daily; but satisfactory results are obtained even with one weekly application. The individual dose to be used for each treatment is not critical. Undesirable side effects were not observed. The oily appearance of the hair is reduced and renewed oiliness is delayed, which makes normal hair grooming possible. A lasting improvement in the appearance of the skin is possible with regular applications according to the invention in the form of skin creams or milk preparations or shaking mixtures.

The following examples shall explain the subject of the invention in more detail.

EXAMPLES

First, the preparation of the arylmercapto-alkanoic acid derivatives is explained with several examples.

1. 2-(4-Chlorophenylmercapto)-Isobutyric Acid Diethylamide 8.4 Grams (36.4 mmol) of 2-(4-chlorophenylmercapto)-isobutyric acid were converted to the acid chloride with 13 g of thionyl chloride in 30 ml toluene. After removing the volatile components by distillation, this acid chloride was taken up in ether (80 ml) and reacted with 8 g of diethylamine. The mixture was agitated for 1 hour at room temperature and 1 hour at the boiling temperature, filtered after the addition of more ether, treated with activated charcoal and evaporated. The residue (10.4 g=100% of theory) yielded 8.5 g (82% of theory) 2-(4-chlorophenylmercapto)-isobutyric acid diethylamide with a boiling point of 114° C./0.01 mbar and a refractive index $n_D^{20}$: 1.5575.

2. Ethyl Ester of 5-Chlorobenzoxazol-2-yl-mercaptoacetic Acid

To the sodium ethylate solution prepared with 250 ml of ethanol and 7.5 g (0.326 mol) of sodium were added 60 g (0.323 mol) of 5-chloro-2-mercaptobenzoxazol, and 59.4 g (0.356 mol) of ethyl bromoacetate were added dropwise with agitation. After boiling for 2 hours, filtering and cooling, 27 g of the ethyl ester of 5-chlorobenzoxazol-2-yl-mercaptoacetic acid with a melting point of 69° to 72° C. precipitated. An additional 28 g (together 63% theor. ester with a melting point of 67°–69° C. were obtained by evaporation of the mother liquor and recrystallization from n-hexane activated charcoal. The following compounds were obtained by analogous procedure:

3. Ethyl Ester of 4-Chlorophenylmercaptoacetic Acid
BP 140° C./0.25 mbar, $n_D^{20}$: 1.5594

4. Ethyl Ester of 2-(4-Chlorophenylmercapto)-Propionic Acid
BP 100° C./0.26 mbar, $n_D^{20}$: 1.5454

5. Ethyl Ester of 2-(4-Chlorophenylmercapto)-Isobutyric Acid
M.p. 42°–45° C.

6. Ethyl Ester of 2,4-Dihydroxyphenylmercaptoacetic Acid
M.p. 43°–46° C. $n_D^{20}$: 1.5650

7. Ethyl Ester of 2,4-Dihydroxyphenylmercapto isobutyric Acid
M.p. 103°–105° C.

8. Ethyl Ester of Benzothiazol-2-yl-mercaptoacetic Acid
M.p. 40°–41° C.

9. Ethyl Ester of Benzimidazol-2-yl-mercaptoacetic Acid
M.p. 95°–96° C.

10. Ethyl Ester of 2-Pyridylmercaptoacetic Acid
BP 92° C./0.07 mbar, $n_D^{20}$: 1.5547

11. Ethyl Ester of 4-Pyridylmercaptoacetic Acid
BP 108° C./0.22 mbar, $n_D^{20}$: 1.5544

12. Ethyl Ester of 4-N-oxide-pyridylmercaptoacetic Acid
BP 141° C./0.04 mbar, $n_D^{20}$: 1.5740

13. Ethyl Ester of p-Acetamidophenylmercaptoacetic Acid
BP 203° C./0.16 mbar, $n_D^{20}$: 1.5775

The antiseborrheic action of the compounds used in the cosmetic preparations according to the invention was subjected to closer scrutiny in subsequent animal experiments. Male Wistar rats weighing 220–230 g were used as experimental animals. The degree of brown discoloration on the shaved backs of the rats was visually evaluated. The brown discoloration is caused by the brown skin surface lipid of the rats. This test is based on the observation that young female rats as well as male rats after washing with tenside solution or a lipolytic solvent, and also male rats that had been systemically treated with estrogen, have only normal, fair, pink-colored skin showing after shaving; in keeping with this observation, comparatively negligible amounts of lipid can be extracted from the shaved hair.

For the evaluation of the sebosuppressive effect, the test substances were applied each in the form of a 1% solution in ethanol or ethanol/acetone (1:1) by brushing unilaterally on the back hair of groups of six rats. The other side was treated only with the solvent minus active substance (control side).

During the 14 days of testing, one daily application was made on a total of nine days. A group of six rats that remained completely untreated was used as additional control. At the end of the testing, the animals were shaved on backs and flanks, and independently visually examined under double blind conditions by an evaluating panel (6 persons).

The first criterion was the evaluation of the correct identification of the treated side by the majority of the panelists. The following differentation was made:

| Symbol | Percentate of panelists who recognized an effect |
| --- | --- |
| + + | 100% |
| + | >50%, 100% |
| 0 | ≦50% |

The second criterion was the determination of the difference between right and left side, for which 1 point could be given per panelist and animal, the darker side being graded 1, the lighter side 0, and in the case of uniform appearance, both sides 0.5 each.

The third criterion was the additional classification of the differences in the intensity of the brown coloring, using the following scale:

3 points dark brown
2 points medium brown
1 point weakly brown
0 points no brown discoloration Significant differences between untreated and treated side in the second method of evaluation indicate the topical effectiveness of a substance. The third method of evaluation is used to form the differences of the sums of points between the untreated control animals and respectively the treated and untreated sides of the experimental animal groups, significant differences between control animals and the treated side of the experimental animals again denoting the action of a substance.

Parallel to the above, a distinct difference between the untreated and the treated side of the experimental animal groups usually can be seen. But this difference is not always as distinct as that between control animals and treated side, which may have different reasons, such as mechanical transfer of substance from one side to the other, or influence of the solvent. The following plan was used for the differentiation of the effects according to the evaluation methods 2 and 3.

| Symbol | Point difference |
|---|---|
| ++ | very large (>99.9% probability) |
| + | significant (≧95% probability) |
| (+) | pronounced but <95% probability |

The results of the evaluation by the above-mentioned plan for the tested substances are compiled in the following table.

| Evaluation of the Sebosuppressive Effects | | | |
|---|---|---|---|
| Substance according to example | Method of evaluation | | |
| | 1 | 2 | 3 |
| 1 | ++ | ++ | (+) |
| 2 | ++ | ++ | ++ |
| 3 | + | ++ | ++ |
| 4 | . | . | . |
| 5 | + | (+) | (+) |
| 6 | . | . | . |
| 7 | . | . | . |
| 8 | + | (+) | (+) |
| 9 | + | (+) | (+) |
| 10 | + | + | ++ |
| 11 | + | ++ | ++ |
| 12 | + | ++ | ++ |
| 13 | ++ | ++ | ++ |
| N,N—diethyl m-toluamide (DE-OS 1906 665) | + | (+) | (+)-0 |
| S—Carboxymethyl-cysteine (DE-OS 16 67903) | 0 | 0 | 0 |

Following are examples of topical agents according to the invention for the treatment of very oily hair and seborrheic skin.

| | Parts by weight |
|---|---|
| Shampoo for Oily Hair | |
| Ammonium lauryl sulfate with 33–35% wash-active substance | 40.0 |
| Diethanolamide of acid of coconut oil | 3.0 |
| Sodium chloride | 2.0 |
| Sodium sulfate | 2.0 |
| Compound according to Example 1 | 5.5 |
| Preservative | 0.1 |
| Perfume oil | 0.1 |

| | Parts by weight |
|---|---|
| Water | 47.4 |
| Hair Treatment | |
| Tegin M$^{(R)}$ (glyceryl mono- and distearate) | 0.7 |
| Cationic tenside | 2.0 |
| Cholesterol | 0.2 |
| Soy lecithin | 0.3 |
| Emulgade A$^{(R)}$ (mixture of cetyl-stearyl) alcohol with nonionic emulsifying agents) | 8.0 |
| Perfume oil | 0.3 |
| Compound according to Example 2 | 7.0 |
| Water, completely demineralized | 81.5 |
| Skin Cream | |
| Self-emulsifying mixture of mono-diglycerides of higher saturated fatty acids with potassium stearate$^{(R)}$ Dehydag | 16.0 |
| Cetyl-stearyl alcohol with approx. 12 mols ethylene oxide | 1.0 |
| 2-Octyldodecanol | 6.0 |
| Isopropyl myristate | 4.0 |
| Glycerol | 6.0 |
| Compound according to Example 2 | 7.0 |
| Water | 60.0 |

We claim:

1. A method for reducing sebaceous cell sebum production in a mammal in need thereof which comprises contacting said sebaceous cell in the skin of said mammal to reduce sebum production of with a topical cosmetic preparation comprising an effective amount one compound having the formula

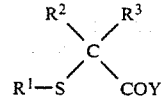

wherein $R^1$ is selected from the group consisting of phenyl, $C_{1-4}$-alkylphenyl, halophenyl, hydroxyphenyl, $C_{1-4}$-alkoxyphenyl, aminophenyl, acetamidophenyl, naphthyl, diphenyl; $R^2$ and $R^3$, independently, are selected from the group consisting of hydrogen and $C_{1-4}$-alkyl; and Y is $-NR^4R_5$, wherein $R^4$ and $R^5$, independently, are selected from the group consisting of hydrogen, $C_{1-6}$-alkyl, $C_{2-3}$-hydroxyalkyl, benzyl, anilyl, and taken together piperidinyl and morpholinyl.

2. The method of claim 1 wherein $R^4$ and $R^5$, independently, are selected from the group consisting of hydrogen, $C_{1-6}$-alkyl and $C_{2-3}$-hydroxyalkyl.

3. The method of claim 2 wherein said compound is 2-(4-chlorophenyl-mercapto)-isobutyric acid diethylamide.

* * * * *